(12) United States Patent (10) Patent No.: US 7,776,324 B2
Nesaretnam et al. (45) Date of Patent: Aug. 17, 2010

(54) CANCER VACCINE

(75) Inventors: Kalanithi Nesaretnam, Kajang (MY); Sitti Rahma Abdul Hafid, Kajang (MY); Kanga Rani Selvaduray, Kajang (MY); Tan Sri Datuk Dr. Yusof Basiron, Kajang (MY)

(73) Assignee: Malaysian Palm Oil Board (MPOB), Kajang (MY)

( * ) Notice: Subject to any disclaimer, the term of this patent is extended or adjusted under 35 U.S.C. 154(b) by 309 days.

(21) Appl. No.: 11/670,967

(22) Filed: Feb. 3, 2007

(65) Prior Publication Data

US 2007/0231351 A1 Oct. 4, 2007

(30) Foreign Application Priority Data

Feb. 3, 2006 (MY) ............................... PI 20060439

(51) Int. Cl.
*A61K 39/39* (2006.01)
*A61K 47/44* (2006.01)
*A61K 35/12* (2006.01)
*A61K 35/28* (2006.01)
*C12N 5/06* (2006.01)

(52) U.S. Cl. ................. 424/93.7; 424/277.1; 424/283.1; 424/573

(58) Field of Classification Search ........................ None
See application file for complete search history.

(56) References Cited

U.S. PATENT DOCUMENTS 6,458,585 B1 * 10/2002 Vachula et al. .............. 435/325

2006/0241174 A1 * 10/2006 Mueller et al. .............. 514/458

FOREIGN PATENT DOCUMENTS

WO WO 03/049755 * 6/2003
WO WO 2004/050855 * 6/2004

OTHER PUBLICATIONS

Abstract of Wheeler (Salud p'ublica de M'exico, (Jul.-Aug. 1997) 39 (4) 283-7).*
Efferson et al (Anticancer Research, 2005, vol. 25, pp. 715-724).*
Bachman et al (Journal of Immunology, 2005, vol. 175, pp. 4677-4685).*
Khanna et al (Journal of Biological Chemistry, 2003, vol. 278, pp. 43508-43515).*
Sigma Cat , 1997, Item No. T-3251, p. 1024).*
Le Fur et al (PNAS, 1997, vol. 94, pp. 7561-7565).*
Abstract of Ramel et al, Environmental Science Research, 1984, vol. 31, pp. 97-112).*

* cited by examiner

*Primary Examiner*—Karen A Canella
(74) *Attorney, Agent, or Firm*—Workman Nydegger

(57) ABSTRACT

The present invention relates to a method for producing a composition for use as a vaccine for treatment or prevention of cancer. The method includes the steps of isolating dendritic cells from a blood, bone marrow or other tissue sample of a patient suffering from cancer or from an unrelated donor, culturing the dendritic cells under conditions and pulsing the dendritic cells with tumour cell lysate or an antigen released by the type of tumour cell and a tocotrienol.

18 Claims, 2 Drawing Sheets

CANCER VACCINE

FIELD OF INVENTION

The present invention relates to a cancer vaccine.

BACKGROUND OF INVENTION

Several types of vaccines are used for the prevention of infectious diseases such as certain tumours, including attenuated microorganisms, recombinant proteins and DNA vaccines. The cell-mediated arm of the immune system is the main arm involved in providing the host with the ability to defend, recover from viral infections and to prevent further infections by the same virus. This type of immune response is also crucial in protecting the host against the onset, development and spread of tumour.

Recently, research has been carried out on the development of vaccine immunotherapy for cancer patients in order to improve the treatment modalities. This form of immunotherapy involves the use of dendritic cells, which are shown to be potent antigen presenting cells. These cells possess unique properties that allow them to elicit primary and boost secondary immune responses as well as regulate the type of T-cell mediated immune response that is induced. In recent years, several studies have demonstrated that tumour antigen-pulsed dendritic cells are capable of inducing both the generation and proliferation of T-helper and cytotoxic T lymphocyte (CTL) cells via antigen presentation by major histocompatibility complex (MHC) class I and class II molecules respectively to mediate tumour immunity.

SUMMARY OF INVENTION

Accordingly, there is provided a method for producing a composition for use as a medicament for treatment or prevention of cancer, the method including the steps of (a) culturing dendritic cells isolated from a patient, under conditions conducive for their growth and proliferation such as conditions suitable for the growth and survival of mammalian cells, on or in a nutrient-rich medium which contains nutrients suitable for the survival and growth of mammalian cells, (b) pulsing said dendritic cells with lysate or a species-defining antigen from a cancerous cell line, and a tocotrienol, under culture and environmental conditions suitable for the survival and growth of the mammalian cells and (c) containing the pulsed dendritic cells in a solid or liquid form suitable for administration to a patient in need thereof.

The present invention consists of several novel features and a combination of parts hereinafter fully described and illustrated in the accompanying drawings, it being understood that various changes in the details may be made without departing from the scope of the invention or sacrificing any of the advantages of the present invention.

BRIEF DESCRIPTION OF THE ACCOMPANYING DRAWINGS

For the purpose of facilitating and understanding of the present invention, there is illustrated in the accompanying drawings, from an inspection of which, when considered in connection with the following description, the invention, its construction and operation and many of its advantages would be readily understood and appreciated.

DETAILED DESCRIPTION OF THE PREFERRED EMBODIMENTS

Figure 1:
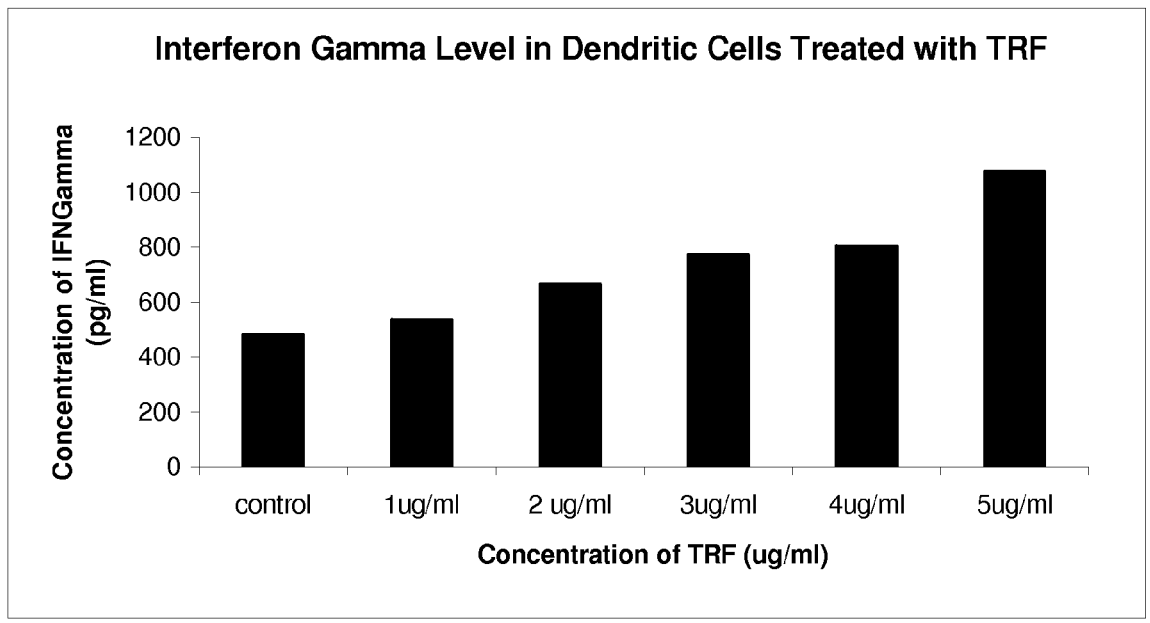
FIG. 1 is a chart showing interferon gamma levels in dendritic cells treated with a tocotrienol-rich fraction (TRF) obtained from a palm oil fruit.

The present invention relates generally to a cancer vaccine. Hereinafter, this specification will describe the present invention according to the preferred embodiments of the present invention. However, it is to be understood that limiting the description to the preferred embodiments of the invention is merely to facilitate discussion of the present invention and it is envisioned that those skilled in the art may devise various modifications and equivalents without departing from the scope of the appended claims.

The composition for use as a vaccine for treatment or prevention of cancer, particularly tumour, is made by a method described hereinafter.

In the preferred embodiment of the present invention, the tumour cell lysate is obtained from a breast cancer cell line, melanoma cell line, lung cancer cell line, prostate cancer cell line, colon cancer cell line, ovarian cancer cell line or a cell line of other histological type. The tumour cell lysate can also be collected from several different lines of tumour cells which shed different but complimentary patterns of tumour antigens so as to broaden the spectrum of tumour antigens in the vaccine preparation.

TRF, a non-toxic natural extract from the oil palm tree fruit, particularly from Tenera species of oil palm tree fruit is used as the preferred tocotrienol. The TRF is found to be highly effective as an adjuvant for enhancing the serum levels of IFN-γ following supplementation in mouse models, and thereby increasing the effectiveness of the dendritic cells in treating mouse mammary cancers. The TRF is simple to isolate and thus can provide a low cost adjuvant to significantly enhance the efficacy of the dendritic cells in treating various types of cancer. It must be appreciated that although the TRF is a preferred tocotrienol, pure tocotrienol can also be used.

Interferons are natural proteins produced by the cells of the immune systems of most animals as a response to challenges by foreign agents such as viruses, bacteria, parasites and tumour cells. Interferons belong to the large class of glycoproteins known as cytokines.

In particular, IFN-γ is a type II subclass produced in activated T cells. IFN-γ is intimately involved in the regulation of mammalian immune and inflammatory responses. It is able to alter transcription in up to 30 genes producing a variety of physiological and cellular responses. This results in anti-viral and anti-tumour effects whilst also acting to potentiate the effects of interferon-alpha (IFN-α) and interferon-beta (IFN-β). IFN-γ is also released by Th1 cells, and recruits leukocytes to a site of infection, resulting in increased inflammation. It also stimulates macrophages to kill bacteria that have been engulfed. The IFN-γ released by Th1 cells is also important in regulating the Th2 response.

Several different types of interferon are now approved for use in humans, and interferon therapy is used (in combination with chemotherapy and radiation) as a treatment for many types of systemic cancer. When used in the systemic therapy, IFN-γ and IFN-γ are mostly administered by an intramuscular injection. The injection of interferons in the muscle, in the vein or under skin is generally well tolerated. It was surprisingly found that serum levels of interferon-gamma (IFN-γ) significantly increased following tocotrienol supplementation in our mouse models.

The vaccine containing dendritic cells or other types of cells able to present antigens directed to a particular tumour type may be used for the prevention or treatment of cancer in humans by administering the vaccine to a patient several times for one or two months, and then once every one to three months (or less) depending on the particular disease being treated, for an extended period of time.

Although, the vaccine is primarily researched for the production of a breast cancer antigen vaccine, however, this invention is also applicable to the production of a human lung cancer vaccine, a human melanoma vaccine, a human colon cancer vaccine and other human cancer vaccines.

The following example is intended to further illustrate the invention, without any intent for the invention to be limited to the specific embodiment described therein.

Cell Preparation

BALB/c mice aged 5-6 weeks old were purchased from the Institute for Medical Research (IMR), Kuala Lumpur. Mice were sacrificed and muscle tissues removed with gauze from the femur and tibias. Then, bones were placed in 60 mm dish with 70% ethanol for 1 minute, washed with RPMI 1640 medium before transferring into fresh medium. Bone marrow cells were isolated by flushing femurs and tibias with 5 ml of same medium by using a syringe. The cells were centrifuged and re-suspended in complete medium (RPMI 1640 supplemented with 10% fetal bovine serum, 1% glutamine and 1% penicillin or streptomycin) to culture the cells.

Generation of Dendritic Cells

Bone marrow cells were harvested from flushed marrow cavities of femurs and tibiae under aseptic conditions and cultured in T25 flasks with 100 units/ml granulocyte macrophage colony-stimulating factor and 100 units/ml interleukin 4 (Peprotech, Rocky Hill, N.J.) at $10^6$ cells/ml in complete media (RPMI 1640 containing 10% heat-inactivated FBS, 0.1 mM nonessential amino acids, 1 μM sodium pyruvate, 2 mM L-glutamine, 100 μg/ml streptomycin, 100 units/ml penicillin, 0.5 μg/ml fungizone, and $5×10^{-5}$ M 2-mercaptoethanol). Cytokines were replenished on day 4. On day 6 of culture, dendritic cells were collected and cultured at $10^6$ cells/ml with granulocyte macrophage colony-stimulating factor and interleukin 4 with or without the addition of 10 ng/ml of recombinant human TGF-$β_1$ (R&D Systems, Minneapolis, Minn.) for 6 days. Dendritic cells were matured with 200 units/ml of TNF-α (Peprotech) for 48 hours.

FACS Analysis

All antibodies used were purchased from Becton Dickinson. For analysis of dendritic cells, samples were stained with FITC-conjugated anti-CD11c. Cells were analyzed using a FACSCalibur flow cytometer (Becton Dickinson Immunocytometry Systems, San Jose, Calif.).

Preparation of Tumour Lysate

The mouse mammary breast cancer cell line, 4T1 was cultured in a T25 $cm^2$ flask with RPMI 1640 medium supplemented 10% fetal bovine serum, 1% penicillin-streptomycin and 1% glutamine. The cells were incubated at 37° C. in a 5% $Co_2$ incubator. For TRF treatment, confluent cells were treated with 8g/ml of TRF (Tocotrienol Rich Fraction, Carotech) for 3 days. A tumour lysate was made by subjecting the cells to two freeze/thaw cycles from—80° C. to 25° C. GM-CSF, IL-4 and TNF-α were added to the lysate at the same concentration as that of dendritic cells culture. The lysate was added to plated dendritic cells and pulsed overnight at 37° C. The dendritic cells were pulsed with tumour lysate were then collected and centrifuged at 2000 rpm for 5 minutes, washed three times with 1× PBS solution and re-suspended in complete medium before injecting into mice.

Treatment of Mice

Six-week-old BALB/c mice were orthotopically injected with $10^4$ 4T1 tumour cells into the mammary gland. The dendritic cells were pulsed with 4T1 tumour cell lysate at a ratio of 1:1 tumour cell equivalents/dendritic cell for 24 hours. After pulsing, the dendritic cells were matured with 200 units/ml of TNF-α for 48 hours. Mice were injected locally (i.t.) with $1.5 ×10^6$ tumour cell lysate-pulsed, matured dendritic cells in 50 μl of PBS on day 15 when tumours were palpable. Vaccination was repeated on days 20 and 25. Primary tumours were measured using vernier calipers.

Experimental Design

Each Batch consists of 4 groups of mice:

Group 1: Only injected with 4T1

Group 2: 4T1+Dendritic Cells pulsed with tumour lysate

Group 3: 4T1+Dendritic cells pulsed with tumour lysate+TRF

Group 4: Injected with dendritic cells

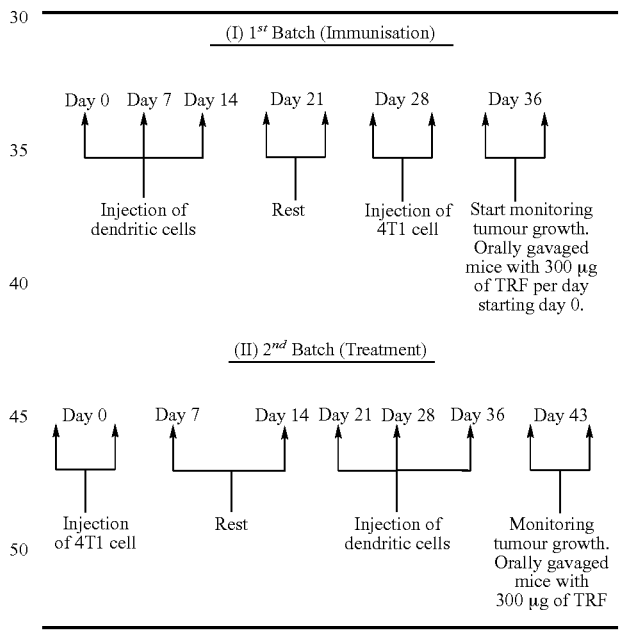

Purification of Dendritic Cells Using Mini Macs Magnetic Beads

Dendritic cells were gently scrapped and centrifuged at 1000 g for 10 minutes at room temperature and re-suspended into 90μL buffer (PBS pH 7.2 supplemented with 2 mM EDTA and 0.5% BSA). 10 μL of CD 11c microbeads were added to the dendritic cells and incubated for 15 minutes at 40° C. The column was washed with 500 μL of buffer before dendritic cells separation. Column was washed three times with buffer to remove the negative fractions. The column was removed from the magnet and dendritic cells were eluted with 1 ml of buffer.

Results
1) Dendritic cells were successfully obtained and grown from mouse bone marrow.
2) Pure dendritic cells were isolated using the mini macs kit.
3) Cytokines were measured in dendritic cells incubated with TRF. There was a linear increase in IFN-γ compared to control cells at the concentrations tested (1-5 μg/ml).
4) Tocotrienol—supplemented dendritic cells that are pulsed with 4T1 mammary gland tumour lysate inhibited the growth of widespread and metastatic breast tumour in mouse models.
5) Tumours that developed in control mice were bigger than in mice injected with dendritic cells.

Figure 2:
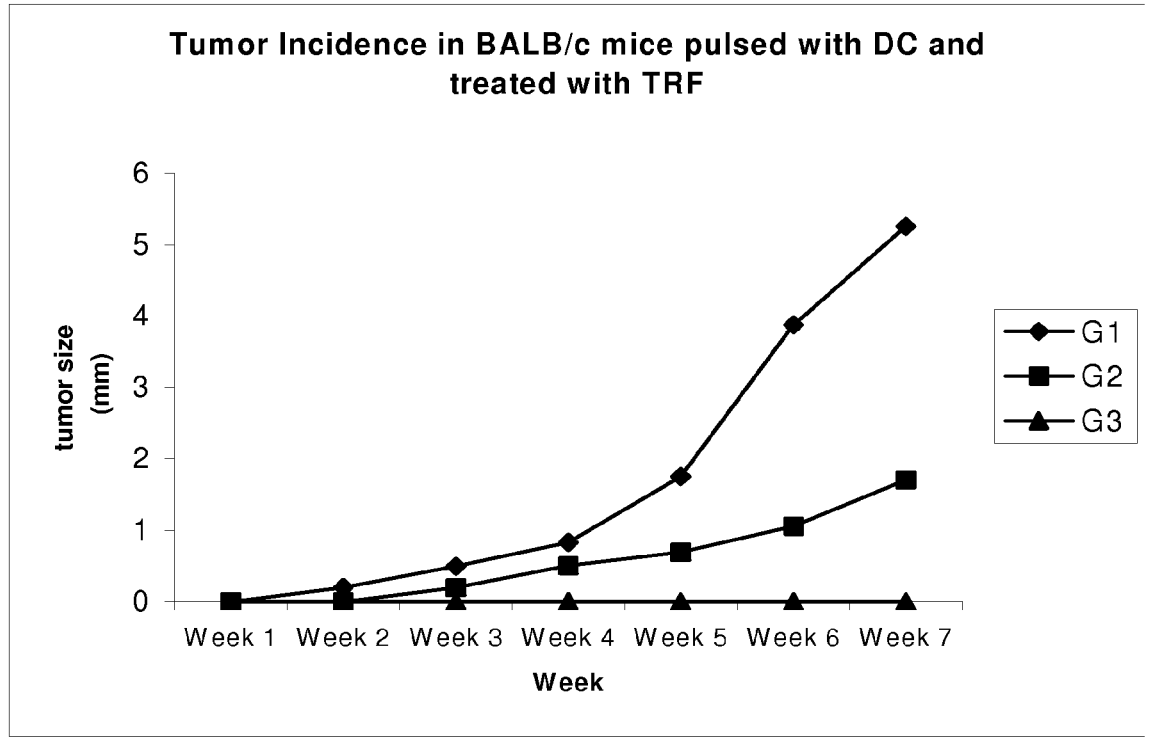
FIG. 2 is a chart showing tumour incidence in BALB/c mice pulsed with dendritic cells and treated with the TRF.
Figure 3:
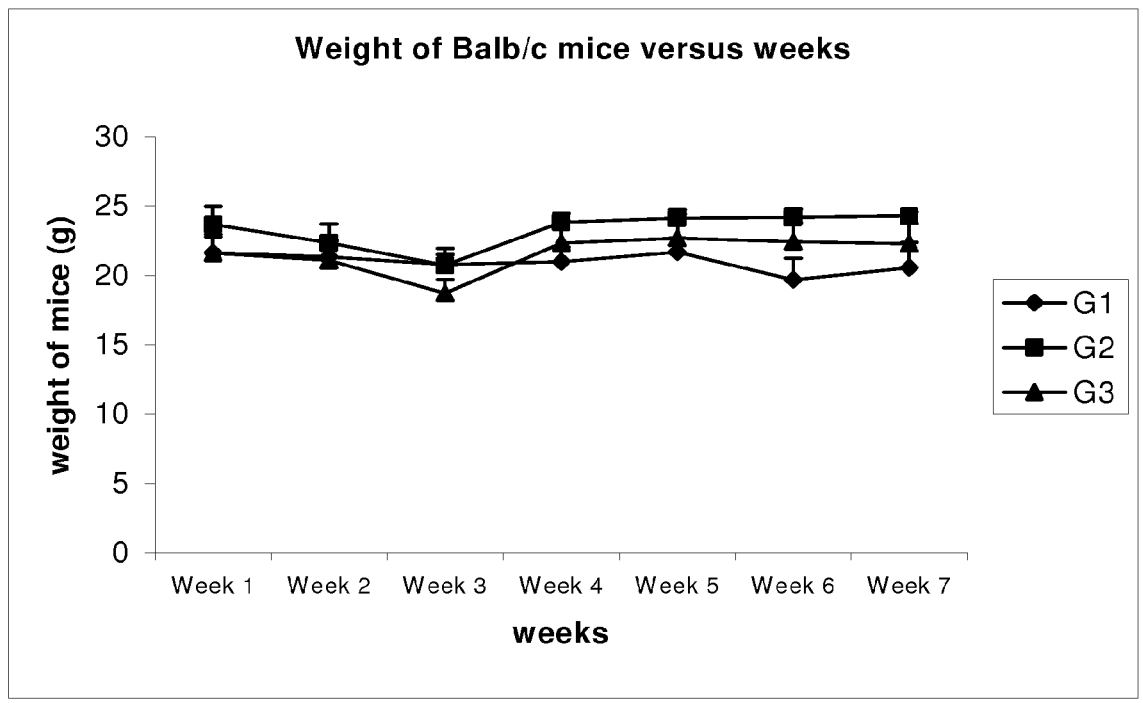
FIG. 3 is a chart showing weight of BALB/c mice versus weeks.
Figure 4:
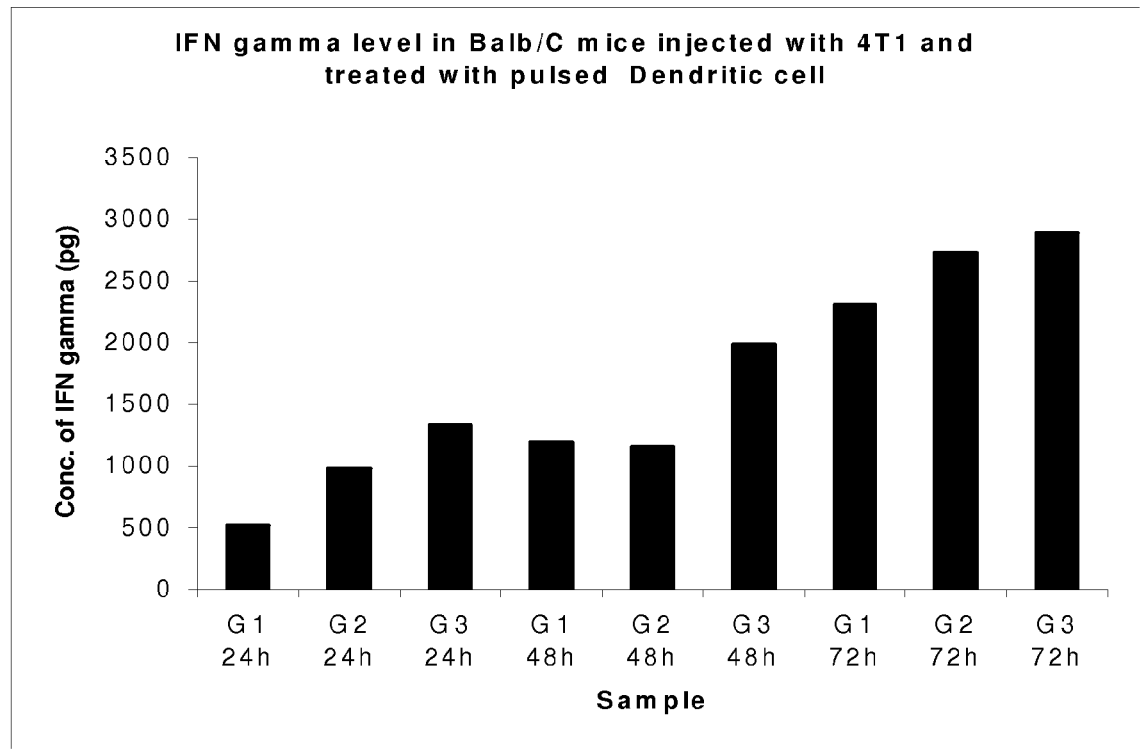
FIG. 4 is a chart showing interferon-gamma (IFN-γ) levels in BALB/c mice injected with 4T1 and treated with pulsed dendritic cells.

The results are shown in the accompanying drawings FIGS. 1 to 4.

The invention claimed is:

1. A method for producing a composition for use as a medicament for treatment of cancer, the method including the steps of:
   a) culturing dendritic cells isolated from a patient, under conditions conducive for their growth and proliferation such as conditions suitable for the growth and survival of mammalian cells, on or in a nutrient-rich medium which contains nutrients suitable for the survival and growth of mammalian cells;
   b) pulsing said dendritic cells with a cancerous cell lysate and with a tocotrienol, under culture and environmental conditions suitable for the survival and growth of mammalian cells; and
   c) containing the pulsed dendritic cells in a solid or liquid form suitable for administration to a patent in need thereof.

2. A method in accordance with claim 1, wherein the dendritic cells are cultured at 36-38° C.

3. A method in accordance with claim 2, wherein the culture medium used is RPMI 1640 containing 10% heat-inactivated FBS, 0.1 mM nonessential amino acids, 1 μM sodium pyruvate, 2 mM L-glutamine, 100 μg/ml streptomycin, 100 units/ml penicillin, 0.5 μg/ml fungizone, and $5 \times 10^{-5}$ M 2-mercaptoethanol.

4. The method as claimed in claim 1, wherein the dendritic cells are cultured at 37° C.

5. A method in accordance with claim 1, wherein the dendritic cells were harvested from flushed marrow cavities of femurs and tibiae under aseptic conditions and cultured in T25 flasks with 100 units/ml granulocyte macrophage colony-stimulating factor and 100 units/ml interleukin 4 at $10^6$ cells/ml in complete media (RPMI 1640 containing 10% heat-inactivated FBS, 0.1 mM nonessential amino acids, 1 μM sodium pyruvate, 2 mM L-glutamine, 100 μg/ml streptomycin, 100 units/ml penicillin, 0.5 μg/ml fungizone, and $5 \times 10^{-5}$ M 2-mercaptoethanol).

6. A method in accordance with claim 1, wherein the dendritic cells are matured with 200 units/ml TNF-α for 48 hours prior to exposure to the tocotrienol.

7. A method as in claim 1, wherein the pulsing is performed on the dendritic cells with a cancerous cell lysate from a cancerous cell line and the tocotrienol.

8. A method in accordance with claim 1, wherein the cancerous cell lysate is obtained from a breast cancer cell line, melanoma cell line, lung cancer cell line, prostate cancer cell line, colon cancer cell line, ovarian cancer cell line or a cell line of other histological type.

9. A method in accordance with claim 1, wherein the cancerous cell lysate is obtained from a breast cancer cell line.

10. A method in accordance with claim 1, wherein the tocotrienol is obtained from palm oil fruit.

11. A method in accordance with claim 10, wherein the tocotrienol acts as an adjuvant to enhance serum levels of interferon-gamma (IFN-γ) in a patient suffering from cancer.

12. A method in accordance with claim 1, wherein the dendritic cells present tumour antigens to the patient's immune system.

13. A method as in claim 1, wherein the composition is formulated for administration as a medicament for treatment of cancer.

14. A method as in claim 1, wherein the tocotrienol is provided in an effective amount to increase serum levels of IFN-γ.

15. A method of treating cancer in a patient comprising, administering a therapeutically effective amount of the composition made in accordance with claim 1 to the patient.

16. A method in accordance with claim 15, wherein the cancer is a tumour.

17. A method in accordance with claim 15, wherein the dendritic cells present tumour antigens to the patient's immune system.

18. A method of enhancing serum levels of interferon-gamma (IFN-γ) in a patient suffering from cancer comprising, administering a therapeutically an effective amount of the composition made in accordance with claim 1 as an adjuvant so as to enhance serum levels of interferon-gamma (IFN-γ) in the patient.

* * * * *